United States Patent
Sanz Balsa (10) Patent No.: US 12,263,240 B1
(45) Date of Patent: Apr. 1, 2025

(54) SINGLE-DOSE COSMETIC PRODUCT AND PROCESS OF MANUFACTURING THEREOF

(71) Applicants: BIOFACTORIA NATURAE ET SALUS SA, Valladolid (ES); Juan Manuel Sanz Balsa, Valladolid (ES)

(72) Inventor: Juan Manuel Sanz Balsa, Valladolid (ES)

(73) Assignees: BIOFACTORIA NATURAE ET SALUS SA, Valladolid (ES); Juan Manuel Sanz Balsa, Valladolid (ES)

( * ) Notice: Subject to any disclaimer, the term of this patent is extended or adjusted under 35 U.S.C. 154(b) by 0 days.

(21) Appl. No.: 18/730,659

(22) PCT Filed: Feb. 9, 2023

(86) PCT No.: PCT/EP2023/053200
§ 371 (c)(1),
(2) Date: Jul. 19, 2024

(87) PCT Pub. No.: WO2023/156286
PCT Pub. Date: Aug. 24, 2023

(30) Foreign Application Priority Data

Feb. 21, 2022 (EP) .................................... 22382143

(51) Int. Cl.
*A61K 8/9794* (2017.01)
*A61K 8/02* (2006.01)
(Continued)

(52) U.S. Cl.
CPC .......... *A61K 8/9794* (2017.08); *A61K 8/0216* (2013.01); *A61K 8/602* (2013.01);
(Continued)

(58) Field of Classification Search
None
See application file for complete search history.

(56) References Cited

U.S. PATENT DOCUMENTS 5,387,415 A * 2/1995 Wunderlich ......... A61K 8/9717
424/464

FOREIGN PATENT DOCUMENTS

CN 1575803 A 2/2005
EP 1543727 A1 6/2005
(Continued)

OTHER PUBLICATIONS

International Search Report and Written Opinion for Corresponding International Application No. PCT/EP2023/053200, 9 pages, Apr. 24, 2023.

*Primary Examiner* — Dominic Lazaro
(74) *Attorney, Agent, or Firm* — LUCAS & MERCANTI, LLP (57) ABSTRACT

A single-dose cosmetic product and process of manufacturing thereof. The single-dose cosmetic product contains a solid portion of parenchyma of an aloe vera plant, a coating with waxy properties completely enclosing the solid portion and at least one tear tape located between the coating and the solid portion. The cosmetic product allows a better handling and application of the aloe vera and also preserves the properties and stability of a 100% aloe vera product without the use of additives. The manufacturing process of this cosmetic product allows the properties of the aloe vera parenchyma to remain intact.

10 Claims, 3 Drawing Sheets

(51) Int. Cl.
  *A61K 8/60* (2006.01)
  *A61K 8/92* (2006.01)
  *A61Q 19/00* (2006.01)
(52) U.S. Cl.
  CPC ............... *A61K 8/92* (2013.01); *A61Q 19/00* (2013.01); *A61K 2800/87* (2013.01)

(56) References Cited

FOREIGN PATENT DOCUMENTS

| | | | | |
|---|---|---|---|---|
| EP | 1543727 B1 * | 3/2007 | ........... | A23C 19/166 |
| EP | 3067060 A1 | 9/2016 | | |
| JP | 2003252719 A | 9/2003 | | |
| WO | 9313754 A1 | 7/1993 | | |
| WO | 9710834 A1 | 3/1997 | | |
| WO | 2009112558 A2 | 9/2009 | | |

* cited by examiner

SINGLE-DOSE COSMETIC PRODUCT AND PROCESS OF MANUFACTURING THEREOF

CROSS-REFERENCE TO RELATED APPLICATIONS

This application is a 371 of PCT/EP2023/053200, filed Feb. 9, 2023, which claims the priority from European Patent Application No. 22382143.0, filed Feb. 21, 2022, the contents of each of which are incorporated herein by reference

Field of the Invention

The present invention relates to cosmetic products. In particular, the present invention relates to a single-dose cosmetic product comprising a solid portion of parenchyma of an aloe vera plant and a coating with waxy properties completely enclosing the solid portion.

The invention also relates to the manufacturing process for said cosmetic product.

Background Art

*Aloe vera* belongs to the Asphodelaceae family of plants. It is a succulent, tender plant containing a high-water content (approx. 99-99.5%). Solid content ranges from 0.5-1% and consists of a variety of active components such as fat and water soluble minerals, vitamins, simple/complex polysaccharides, organic acids, enzymes, and phenolic compounds.

Its succulent leaves arranged in a rosette are composed of three layers, the external one, composed of the bark or exocarp which represents 20 to 30% of the weight of the whole plant and is green or bluish-green in color; the central one called parenchyma, also known as fillet, pulp or gel, which is transparent and has a gelatinous and fibrous matrix and represents 50 to 60% of the total weight of the plant; and between the exocarp and the parenchyma, occupying the entire inner surface of the leaf, there are the aloin ducts, which are a group of longitudinally oriented canals through which the acybar, also called latex, circulates.

*Aloe vera* is well known for its therapeutic potential. A number of beneficial effects of *Aloe vera* have been reported, including immunomodulatory, wound and burn healing, hypoglycemic, anticancer, gastro-protective, antifungal and anti-inflammatory properties. These beneficial therapeutic properties of *Aloe vera* have been employed for several commercial applications.

As a cosmetic ingredient, aloe vera is widely used in many mainstream skincare and cosmetics' products. The plant is very skin-friendly and has a low risk of causing allergies, sensitivity, or skin reactions, and it is also versatile. It is common in after-sun products, and in facial, hair and body care products.

The cosmetic products or compositions that contains a high percentage of aloe vera are always accompanied by other compounds or active ingredients, such as preservatives or antimicrobials and other chemical products that helps to stabilize and preserve the cosmetic product or composition, to prevent the degradation of the properties of aloe vera.

For example, WO2009112558A1 describes a composition to be used as a base for cosmetic products, comprising aloe vera gel from 50% to 99% by weight and an emulsifier comprising an acryloyl laurate copolymer, a non-ionic surfactant consisting of an ester of sorbitol polyethoxylate, and an oil of natural origin.

JP2003252719A relates to a cosmetic product mainly composed of aloe vera gel juice. The product comprises juice of aloe vera gel (between 75-83% by weight), 1,3 butylene glycol, glycerin, and sodium hyaluronate. The active ingredients moisturize the skin, prevent skin spots and freckles, and promote the regeneration of collagen and superoxide degrading enzymes in the skin.

However, the use of some chemical compounds in these compositions can have an adverse effect on the health of the consumer. There is also a growing interest in 100% natural cosmetic products, in which these chemical compounds or other additives are not incorporated.

However, preserving the properties of the compounds in cosmetic products without the use of such chemical compounds is difficult. In the case of aloe vera, all the benefits of aloe are most abundant when the aloe vera product is obtained directly from the plant, but the active ingredients of aloe vera deteriorate over time and preserving all the properties is complex.

One of the methods used to prevent the degradation of the properties and to increase the shelf life of pure aloe vera is to subject the gel of aloe vera to a freezing treatment, as described in EP3067060A1.

EP3067060A1 refers to a process that makes it possible to use a pure aloe vera gel which contains all the natural properties of the plant, based on the incorporation of a stabilization process achieved through freezing, whereby it is possible to topically apply the cold cream, lotion, pomade, or ointment, achieving all the typical uses of aloe vera, though primarily to alleviate all kinds of burns. The gel is stored in individual PET or similar plastic containers, designed to withstand temperatures as low as −19° C. without suffering any damage. The product obtained is a natural aloe vera cold gel without stabilizers.

The disadvantages of EP3067060A1 are as follows. The steps used for the method of obtaining the product, such as crushing and filtering the aloe vera, alter its natural structure and cause the loss of functional molecules of the aloe vera such as polysaccharides, vitamins and minerals. Moreover, this processing results in the loss of the endophytic microorganisms that live in the aloe vera plant tissues.

In addition, the aloe vera gel is subjected to a freezing process, in which the gel is stabilized. However, the freezing process inactivates certain micro-organisms but is not fully effective unless it is combined with other processes (heating, irradiation, acidification, etc.).

Furthermore, storage in such plastic containers does not prevent the aloe vera gel from degrading due to temperature differences, exposure to light, and other storage factors that directly affect shelf life. This last aspect is also affected by the fact that the product must be kept at low temperatures, and this creates difficulties in transport, storage and handling, as special conditions are needed.

Therefore, there is a need to find new cosmetic products based on aloe vera that concentrate all the properties of pure aloe vera and are also stable over time, without the need to incorporate chemical compounds such as stabilizers or preservatives and/or the use of complex manufacturing processes.

SUMMARY OF INVENTION

In view of the problems of the prior art, the main object of the present invention is to provide a single-dose cosmetic product comprising a solid portion of parenchyma of an aloe vera plant, a coating with waxy properties completely enclosing the solid portion and at least one tear tape located between the coating and the solid portion.

The cosmetic product of the present invention solves the technical problem of preserving the properties and stability of a 100% aloe vera product without the use of additives.

The main technical difference compared to a conventional cosmetic product lies in the fact that this new cosmetic product is like applying the 100% pure/natural plant directly to the skin, without other ingredients that dilute its effectiveness, without preservatives, without colourings, without artificial perfumes, without undesirable substances that reduce the quality of the cosmetic.

Another unexpected technical difference is that the cosmetic product of present invention makes it possible to keep alive various endophytic microorganisms that naturally live in the plant, such as the species *Pantoea agglomerans, Yersinia kristensenii, Erwinia billingiae, Rahnella Victoriana, Pantoea allii, Serratia liquefaciens, Yersinia ruckeri, Rahnella woolbedingensis, Leclercia adecarboxylata Serratia grimesii, Rahnella inusitata* and *Pantoea ananatis*. These endophytic microorganisms are natural probiotics that reside in the different plant tissues (parenchyma) and have beneficial effects on the immune system of the skin and on the treatment of skin diseases.

Conventional cosmetic products, whether in the form of gel, cream or ointment, cannot contain these endophytic micro-organisms because the production process to which they are subjected always destroys the aloe plant tissues where these endophytic microorganisms live.

On the other hand, conventional cosmetic products, as mentioned above, are commercially presented in the form of gel, cream, or ointment. The application of these cosmetic products by the user is sometimes inadequate because the product does not allow correct dosage, or the texture of the product is difficult to handle.

The cosmetic product of the present invention is in the form of a natural piece of the plant covered with a coating with waxy properties that allows a better handling of the aloe vera and also preserves its properties. Furthermore, the cosmetic product of the present invention comprises a piece of aloe vera parenchyma which is a suitable amount for a single dose.

Furthermore, the coating with waxy properties facilitates the manipulation of the piece of parenchyma of an aloe vera plant, as it is a slippery product and therefore, its application can be complicated for the user.

The coating with waxy properties has several functions. The coating protects the piece of parenchyma of an aloe vera plant from deterioration by dehydration. Furthermore, the coating forms a physical barrier to micro-organisms, prevents the attachment of micro-organisms to the surface of the piece of parenchyma of an aloe vera plant and reduces the growth of micro-organisms.

In addition, the presence of at least one tear tape aids the use of the cosmetic product. Specifically, the tear tape helps to remove part of the coating, leaving one part of solid portion uncoated and another part still coated. The uncoated solid portion can be applied to any area of the user's body.

In a first aspect, the present invention refers to a single-dose cosmetic product comprising a solid portion of parenchyma of an aloe vera plant, a coating and at least one tear tape, wherein the coating completely enclosing the solid portion and is made of a material with waxy properties selected from the group consisting of hydrocarbon waxes and natural waxes or mixtures thereof, and wherein the tear tape is made of a non-woven material and is located between the coating and the solid portion.

Examples of natural waxes include carnauba wax, candelilla wax, beeswax, Japan wax, rice bran wax and sunflower seed wax. Among the above waxes, beeswax is more preferable.

Examples of hydrocarbon waxes include polyethylene wax, paraffin wax, ceresin, and microcrystalline wax.

Optionally, the coating of the cosmetic product of the present invention further comprises natamycin to prevent fungal contamination of the product. A dose between 3 to 20 ppm may be used.

Optionally, the coating of the cosmetic product of the present invention further comprises at least one synthetic or natural dye. Preferably, the dye is copper chlorophyllin.

In the present invention, *Aloe vera* parenchyma can be extracted from any *Aloe vera* plant, such as *Aloe barbadensis* Miller, *Aloe Arborescens, Aloe Ferox, Aloe vera* (L.) Burn, *Aloe officinalis, Aloe* Vulgaris Lamarck, among others. Preferably, the aloe vera plant is *Aloe barbadensis* Miller.

The tear tape is made of 100% non-woven material. This textile material is flat, porous sheets that is manufactured directly from filaments. It has properties that make it the best choice for its function, among them are its tear strength and its ability to adhere to the coating.

In another embodiment, the single-dose cosmetic product of the present invention further comprises at least one cosmetic active ingredient selected from the group consisting of vitamins, minerals, essential oils and mixtures thereof inserted within the parenchyma.

The insertion of the at least one cosmetic active ingredient within the parenchyma can be done by means of simple diffusion by molecular concentration gradient or by forced diffusion by injection into the parenchyma.

The active ingredient used in the cosmetic composition of the single-dose cosmetic product of the present invention may have a wide variety of purposes and functions. In general, such components will provide or at least are expected to provide some benefit to the user, preferably to the user's skin or hair, such as an anti-aging, cell regenerating, antioxidant, disinfectant, moisturizing, healing effect, among others.

The amount of the active ingredient(s) to be used with the present invention can vary widely depending on the particular application, and all such amounts can be determined by those skilled. For example, amount of the active ingredient (s) may vary depending upon the ability of the ingredient to penetrate through, onto, or into the pores of the skin. Other factors which may influence the relative amount of the active ingredient include the particular active ingredient involved, the particular benefit desired, the sensitivity of the user to the active ingredient, the health condition, age, and skin condition of the user, and the like. In sum, the active ingredient(s) is preferably used in a "safe and effective amount," which is an amount that is high enough to deliver a desired skin benefit.

In a second aspect of the invention, process of manufacturing the single-dose cosmetic product of the first aspect of the invention. The process comprises the following steps:
  (i) cleaning and disinfecting the surface of an aloe vera leaf;
  (ii) removing the cuticle and exocarp of the aloe vera leaf to obtain aloe vera parenchyma;
  (iii) cutting the aloe vera parenchyma into solid portions and macerate the solid portions in a solution of processing aids;
  (iv) eliminating the solution of processing aids from the portions by means of filtration;

(v) attaching at least one tear tape of a non-woven material to each of the solid portions;

(vi) covering the portion with the tear tape of the step (v) with a made of a material with waxy properties selected from the group consisting of hydrocarbon waxes and natural waxes or mixtures thereof; and (vii) applying a high-pressure process to the product obtained in step (vi) to obtain the cosmetic product, wherein the pressure is between 400 MPa and 600 MPa.

In the present invention, "processing aids" are subsidiary technical substances, added indirectly for manufacturing purposes. These substances, which are added to the cosmetic during the manufacturing process in order to keep the raw material stable for the duration of the manufacturing process, are removed from the cosmetic in accordance with good manufacturing practice before it is packaged in its final form. Any person skilled in the art would know how to select said processing aids for this use.

In another embodiment, when the single-dose cosmetic product of the first aspect of the invention further comprises at least one cosmetic active ingredient, there is an additional step before step (iv) consisting of inserting at least one cosmetic active ingredient selected from the group consisting of vitamins, minerals, essential oils and mixtures thereof is inserted within the parenchyma.

The insertion of the at least one cosmetic active ingredient within the parenchyma can be done by means of simple diffusion by molecular concentration gradient or by forced diffusion by injection into the parenchyma.

In the process of the present invention, preferably the time of the high-pressure process of step (vii) is between 3 and 6 minutes. More preferably the time of the high-pressure process of step (vii) is 3 minutes.

Optionally, the process comprises a step (viii) wherein the product obtained in step (vii) is packaged in a stand-up pouch or sealed sachet.

BRIEF DESCRIPTION OF DRAWINGS

The following figures are described below. These illustrate the exemplary embodiments and are not limiting their scope.

DESCRIPTION OF EMBODIMENTS

Example 1. Process of Manufacturing the Cosmetic Product of the Present Invention First of all, a skilled person is aware of suitable apparatus and equipment for carrying out the process in accordance with the present invention and will select the suitable system based on his professional experience, so that no further extensive details need to be given here.

Initially, the coarse dirt was removed from the surface of the aloe vera leaf by immersion in a water immersion tank. Subsequently, disinfection of the aloe vera bark was carried out by immersing the aloe vera leaves for 5 minutes in water and sodium hypochlorite in a ratio (1:3). The aloe vera leaves were then rinsed by immersing them in tanks with water for 3 minutes.

Next, the outer bark of the aloe vera leaf was mechanically brushed in an industrial washing machine and then rinsed with pressurised water jets. The upper and lower parts of the aloe vera leaf were trimmed with cutting blades and then rinsed with pressurised water jets.

Subsequently, the aloe vera leaf was debarked, removing the cuticle and exocarp of the leaf to obtain pieces of aloe vera parenchyma, which were cut into portions (approx. 5×2,5×1.5 cm) using shear blades or high-pressure water jet machinery.

The cut portions of aloe vera parenchyma were subjected to industrial blanching with boiling water (100° C.) for 30-60 seconds. Said portions were then macerated in a solution of processing aids, which allowed the cut portions to be stored for the next 18-20 hours. This maceration helped the pieces of aloe vera parenchyma not to lose physical properties such as colour and texture and also prevented contamination during the storage period.

In this example, the processing aid used was a composition comprising sorbate (0.2-0.4% w/w), benzoate (0.05-0.1% w/w), ascorbic acid (0.1-0.2% w/w), L-cysteine (0.3-0.6% w/w), water (99.35-98.3% w/w) and citric acid (up to pH 3.4).

Subsequently, the solution of technological aids described in the previous step was completely eliminated by means of a gravity filtration for 10 minutes with a perforated mesh. Once the solution of technological aids had been removed, the pieces were separated from each other.

On each piece, a tear tape of non-woven material was attached in the central part of the piece and along the length and width of the piece. The tear tape was not fixed by any means, but simply placed by hand on the surface of the piece.

Later, the portion with the tear tape was covered with a coating with waxy properties. In this example, the coating composition was 70%-80% esters, 10%-15% free acids and 10%-20% paraffins.

The coating was heated at a temperature between 75-100° C. for 2-4 hours until it was completely melted, acquiring a liquid state. The liquid coating was applied to the portion and then a cooling phase was carried out using a cold tunnel system (<14° C.).

Finally, the product obtained in the previous step was treated with high-pressure process to obtain the cosmetic product of the present invention. The pressure of the high-pressure process was 600 MPa for 3 minutes.

Figure 1:
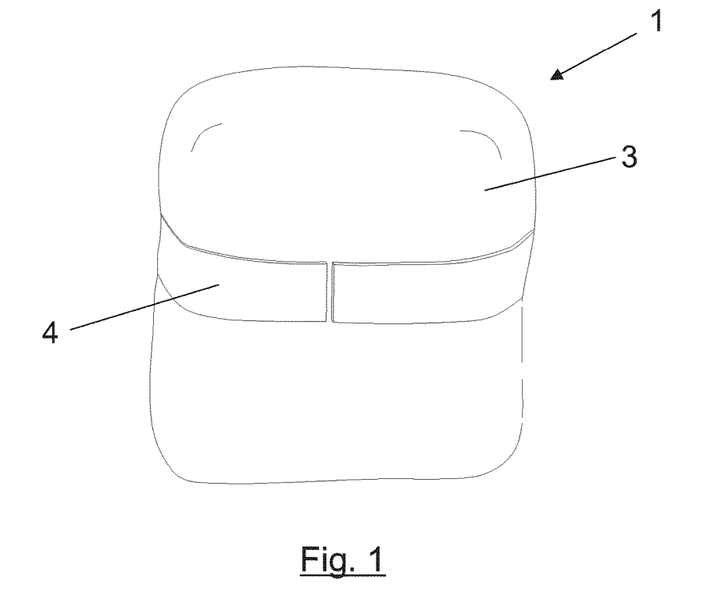
FIG. 1 shows the unopened cosmetic product.
Figure 2:
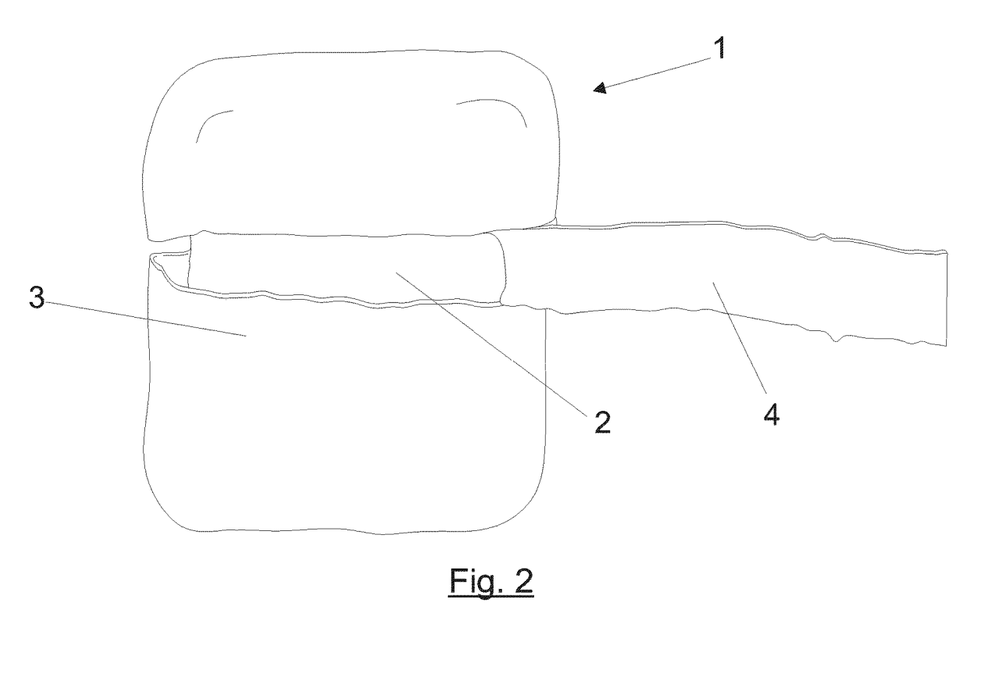
FIG. 2 shows the cosmetic product during the opening process.
Figure 3:
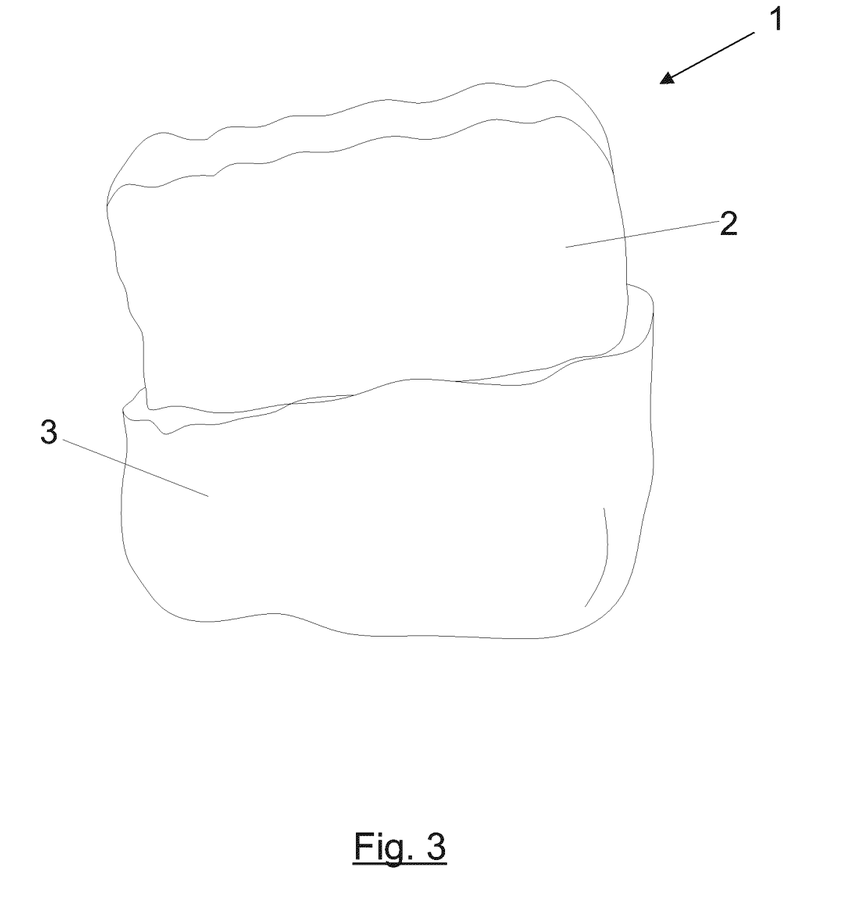
FIG. 3 shows the opened cosmetic product, where part of the coating has been removed and part of the solid portion of parenchyma is exposed for application.

The product obtained is shown in FIG. 1. To use, the user pulls the tear tape, partially removing the coating and exposing part of the solid portion of the parenchyma (FIGS. 2 and 3). The user can then apply the solid portion of parenchyma to the desired area.

Example 2. Comparative Test of the Properties of Commercial Products Containing *Aloe* Vera Against the Cosmetic Product of the Present Invention The beneficial effects of aloe vera are directly related to the active compounds it contains. The methods used to preserve and stabilise the products obtained from aloe vera can have greatly influence in the concentration of these compounds and thus the intensity of the beneficial effect attributed to them.

For this reason, 4 samples of aloe vera in different formats were analysed by High-performance liquid chromatography (HPLC). Table 1 shows the composition of each of the samples.

The concentration of the main compounds of aloe vera: Acemannan (aloverose), glucomannan, mannose and vitamins A and C was analysed in each sample. Table 2 shows the results obtained.

TABLE 1

Ingredients of the samples analysed

| Sample No. | Product | Composition |
|---|---|---|
| 1 | Pure *aloe vera* leaf | 100% *Aloe vera* |
| 2 | Cosmetic product of the present invention | 100% *Aloe vera parenchyma* |
| 3 | *Aloe Vera* Gel | *Aloe barbadensis* leaf juice, water, carbomer, Imidazolidinyl urea, sodium benzoate, sodium hydroxide, potassium sorbate, tridecet-9, hydrogenated castor oil PEG-40, perfume, propylene glycol. |
| 4 | *Aloe Vera* Cream | Water, Cetearyl, Alcohol, Mineral oil, Glycerin, Glyceryl stearate, Ammonium polyacrylate, Isoparaffin C13-16, Laurate-30, *Aloe Barbadensis* leaf extract, Phenoxyethanol, Fragrance, Xanthan gum, Chlorphenesin, sodium acrylate/Acryloyldimethyl sodium, taurate copolymer, Isohexadecane, Polysorbate 80, propylene glycol, octanediol, pentylene glycol, Benzyl salicylate, Butylphenyl methylpropional, linalool, citronella, Hexyl Cinnamal, D-limonene. |

TABLE 2

Concentration of Acemannan (aloverose), glucomannan, mannose and vitamins A and C in the samples analysed

| Compounds (mg/kg) | Sample 1 | Sample 2 | Sample 3 | Sample 4 |
|---|---|---|---|---|
| Acemannan (aloverose) | 1867 | 1875 | 1684 | 233 |
| Glucomannan | 4156 | 4165 | 3742 | 328 |
| Mannose | 2151 | 2151 | 1940 | 184 |
| Vitamin C | 3 | 2.78 | 2,30 | 0.19 |
| Vitamin A | 12.5 | 14 | 10.5 | 1.65 |

Table 3 shows the percentage of each compound present in each type of sample, with respect to the concentration of pure aloe vera (sample 1).

TABLE 3

Percentage of each compound in relation to the concentration of pure *Aloe Vera*

| Compounds (mg/kg) | Sample 1 | Sample 2 | Sample 3 | Sample 4 |
|---|---|---|---|---|
| Acemannan (aloverose) | 100% | 100% | 90.2% | 12.5% |
| Glucomannan | 100% | 100% | 90% | 7.9% |
| Mannose | 100% | 100% | 90.2% | 8.6% |
| Vitamin C | 100% | 92.7% | 76.5% | 6.2% |
| Vitamin A | 100% | <100% | 84% | 13.2% |

The cosmetic product of the present invention presents a concentration more similar to the aloe vera pure (sample 1) of each of the compounds analysed. Specifically, the concentration of the polysaccharides (Acemannan and Glucomannan) and the monosaccharide Mannose is similar to that of the natural product, i.e. these compounds remain intact and have not been affected by processing. Vitamin C has been degraded to a minor extent during processing but maintains 92.7% of the concentration compared to the pure aloe vera (sample 1). On the other hand, the slightly higher concentration of vitamin A (<100%) that sample 2 presents may be due to the heterogeneity between samples, but in any case, it indicates that it is not degraded in the process.

*Aloe Vera* gel (sample 3) reflects a decrease of approximately 10% of saccharides, 23.5% of vitamin C and 16% of vitamin A. In the cream format (sample 4), none of the compounds exceeds 15% of the concentration compared to the pure aloe vera (sample 1).

Additionally, the stability of the cosmetic product of the present invention was evaluated to estimate its shelf life, as well as the degradation over time, compared to commercial products.

Samples 2, 3 and 4 were stored in temperature-controlled chambers (20° C.) and monitored over time. The samples were analysed at the beginning of the study and then periodically every 2 months, until 10 months. The main compounds of aloe vera mentioned above were used for shelf life monitoring. The method of analysis was by high performance liquid chromatography (HPLC). The results obtained are presented in tables 4, 5 and 6, and FIG. 4.

TABLE 4

Percentage of loss of each compound in the cosmetic product of the present invention
Sample 2 (Cosmetic product of the present invention)

| Time (months) | Acemannan (aloverose) (mg/kg) | Glucomannan (mg/kg) | Mannose (mg/kg) | Vitamin C (mg/kg) | Vitamin A (µg/kg) |
|---|---|---|---|---|---|
| 0 | 1874.5 | 4165 | 2150 | 2.78 | 14 |
| 6 | 1871 | 4122 | 2105 | 2.77 | 14 |
| 10 | 1864 | 4118 | 2096 | 2.52 | 13.5 |
| % loss | 0.6 | 1.1 | 2.5 | 9.35 | 3.6 |

TABLE 5

Percentage of loss of each compound in the *aloe vera* gel
Sample 3 (*Aloe Vera* Gel)

| Time (months) | Acemannan (aloverose) (mg/kg) | Glucomannan (mg/kg) | Mannose (mg/kg) | Vitamin C (mg/kg) | Vitamin A (µg/kg) |
|---|---|---|---|---|---|
| 0 | 1683.5 | 3742 | 1940 | 2.30 | 10.50 |
| 6 | 1588 | 3681 | 1852 | 2.30 | 10 |
| 10 | 1493 | 3632 | 1812 | 2.05 | 9.27 |
| % loss | 11.3 | 2.9 | 6.6 | 10.7 | 11.7 |

TABLE 6

Percentage of loss of each compound in the *aloe vera* cream
Sample 4 (*Aloe Vera* Cream)

| Time (months) | Acemannan (aloverose) (mg/kg) | Glucomannan (mg/kg) | Mannose (mg/kg) | Vitamin C (mg/kg) | Vitamin A (µg/kg) |
|---|---|---|---|---|---|
| 0 | 232.5 | 328 | 184 | 0.19 | 1.65 |
| 6 | 229 | 326 | 178 | 0.17 | 1.60 |

TABLE 6-continued

Percentage of loss of each compound in the *aloe vera* cream Sample 4 (*Aloe Vera* Cream)

| Time (months) | Acemannan (aloverose) (mg/kg) | Glucomannan (mg/kg) | Mannose (mg/kg) | Vitamin C (mg/kg) | Vitamin A (µg/kg) |
|---|---|---|---|---|---|
| 10 | 224 | 325 | 172 | 0.15 | 1.52 |
| % loss | 3.7 | 0.9 | 6.5 | 18.9 | 7.88 |

As shown in the tables above, the initial concentration of the compounds analysed was higher in the cosmetic product of the present invention, with respect to the other two products (gel and cream) and mainly with respect to the aloe vera cream, the concentration being around 10 times higher in the cosmetic product of the present invention.

Figure 4:
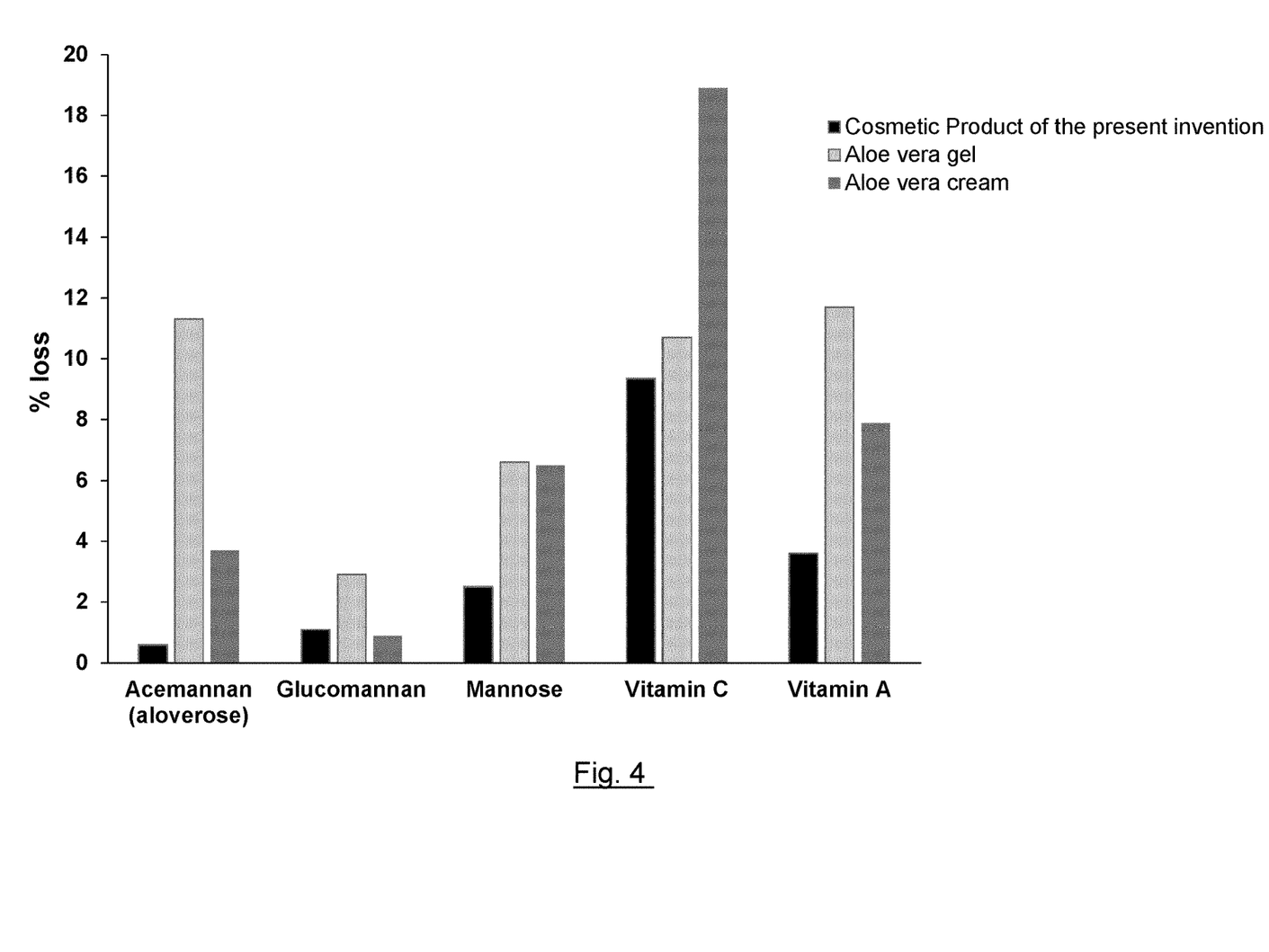
FIG. 4 shows the % loss of each active compound (Acemannan (aloverose), glucomannan, mannose and vitamins A and C), after ten months of storage with respect to its initial concentration, for each of the aloe vera formats analysed (cosmetic product of the present invention, aloe vera gel and aloe vera cream).

Moreover, after ten months of storage, the product of the present invention did not experience a significant loss of any of the analysed compounds, taking into account that the difference between the initial and final concentration of the analysed compounds is lower than the analytical uncertainty (the percentage of loss is not significant) (See FIG. 4).

In contrast, the gel experienced significant losses of vitamin A (11,7%), vitamin C (10,7%) and aloverose (11, 35%) and similarly, the cream has experienced losses of vitamin C (18,9%), vitamin A (7,88%) and mannose (6,5%).

As a conclusion of the tests carried out, the concentration of any of the compounds analysed (active ingredients on the basis of which the health-giving properties of aloe vera are attributed) is higher in the cosmetic product of the present invention than in the gel, and significantly higher than in the aloe vera cream (approx. ten times higher).

Furthermore, the cosmetic product of the present invention maintains the same beneficial properties as pure aloe vera. Furthermore, the cosmetic product of the present invention is presented in single-dose format and has been treated with a high-pressure treatment (physical treatment that maintains the original characteristics of the product), so it does not require the use of preservatives, unlike the other formats.

Another advantage of the product of the present invention is that it is more hypoallergenic than the other formats (gel and cream) as it does not contain any preservatives, which can cause allergic reactions by ingestion or contact.

Example 3. Metagenomic Analysis of the Cosmetic Product of the Present Invention DNA extraction from samples of the product of the present invention was carried out with two different commercial DNA extraction kits: (1) DNeasy UltraClean Microbial kit (Qiagen) and (2) DNeasy PowerLyzer PowerSoil kit (Qiagen).

The DNA obtained was quantified using the Qubit (Thermofisher).

Amplification of the 16S rRNA gene was performed in the samples with the highest amount of DNA. This gene is conserved in all bacterial species, which makes it possible to identify and establish phylogenies between different bacterial species based on differences in the genetic sequences of the gene.

The results obtained revealed that the samples of the cosmetic product of the present invention contained the following 5 genus of bacteria: *Pantoea, Yersinia, Rahnella, Erwinia* and *Serratia*. More specifically, the main species present are *Pantoea agglomerans, Yersinia kristensenii, Erwinia billingiae, Rahnella Victoriana, Pantoea allii, Serratia liquefaciens, Yersinia ruckeri, Rahnella woolbedingensis, Leclercia adecarboxylata Serratia grimesii, Rahnella inusitata* and *Pantoea ananatis*.

These endophytic microorganisms are natural probiotics that reside inside plant tissues (parenchyma). The product of the present invention, by keeping the parenchyma intact, keeps these microorganisms alive, generating a consequent healthy effect on the skin.

In none of the conventional cosmetic products, whether in the form of gel, cream or ointment, is it possible to keep these microorganisms alive due to their production processes, since in order to produce these products, it is essential to "break" or "destroy" the tissues of the aloe plant where the microorganisms live.

The invention claimed is:

1. A single-dose cosmetic product (1) comprising a solid portion of parenchyma of an aloe vera plant (2), a coating (3) and at least one tear tape (4),
   wherein the coating (3) completely enclosing the solid portion (2) and is made of a material with waxy properties selected from the group consisting of hydrocarbon waxes and natural waxes or mixtures thereof, and
   wherein the tear tape (4) is made of a non-woven material and is located between the coating and the solid portion.

2. The single-dose cosmetic product according to claim 1, wherein the coating (3) further comprises natamycin.

3. The single-dose cosmetic product according to claim 1, wherein the coating (3) further comprises at least one synthetic or natural dye.

4. The single-dose cosmetic product according to claim 1, wherein the cosmetic product (1) further comprises at least one cosmetic active ingredient selected from the group consisting of vitamins, minerals, essential oils and mixtures thereof inserted within the solid portion of parenchyma (2).

5. A process of manufacturing the single-dose cosmetic product (1) according to claim 1, comprising the following steps:
   (i) cleaning and disinfecting a surface of an aloe vera leaf;
   (ii) removing the cuticle and exocarp of the aloe vera leaf to obtain aloe vera parenchyma;
   (iii) cutting the aloe vera parenchyma into solid portions (2) and macerate the solid portions (2) in a solution of processing aids;
   (iv) eliminating the solution of processing aids from the portions by means of filtration;
   (v) attaching at least one tear tape (4) of a non-woven material to each of the solid portions (2);
   (vi) covering the solid portion (2) with the tear tape (4) of the step (v) with a coating made of a material with waxy properties selected from the group consisting of hydrocarbon waxes and natural waxes or mixtures thereof; and
   (vii) applying a high-pressure process to the product obtained in step (vi) to obtain the cosmetic product (1), wherein the pressure is between 400 MPa and 600 MPa.

6. The process of manufacturing according to claim 5, wherein before step (v) there is an additional step in which at least one cosmetic active ingredient selected from the group consisting of vitamins, minerals, essential oils and mixtures thereof is inserted within the parenchyma.

7. The process of manufacturing according to claim 5, wherein the pressure of the high-pressure process of step (vii) is 600 MPa.

8. The process of manufacturing according to claim 5, wherein the time of the high-pressure process of step (vii) is between 3 and 6 minutes.

9. The process of manufacturing according to claim 8, wherein the time of the high-pressure process of step (vii) is 3 minutes.

10. The process of manufacturing according to claim 5, wherein the process further comprises a step (viii) wherein the product obtained in step (vii) is packaged in a stand-up pouch or sealed sachet.

* * * * *